United States Patent
Shinbo et al.

[11] Patent Number: 4,942,149
[45] Date of Patent: Jul. 17, 1990

[54] CROWN ETHER COMPOUND AND SEPARATING AGENT

[75] Inventors: Toshio Shinbo, Ibaraki, Japan; Tomohiko Yamaguchi, Dortmund, Fed. Rep. of Germany; Kouzou Tachibana, Hyogo, Japan

[73] Assignees: Director-General of Agency of Industrial Science and Technology, Tokyo; Daicel Chemical Industries, Sakai, both of Japan

[21] Appl. No.: 398,844

[22] Filed: Aug. 25, 1989

[30] Foreign Application Priority Data

Sep. 5, 1988 [JP] Japan ................... 63-221879

[51] Int. Cl.$^5$ ............... B01J 20/26; C07D 323/00
[52] U.S. Cl. ............................. 502/401; 549/349
[58] Field of Search .................... 549/349; 502/401

[56] References Cited

FOREIGN PATENT DOCUMENTS 2730771  1/1978  Fed. Rep. of Germany .

OTHER PUBLICATIONS

Cram et al., "Host–Guest Complexation. 9.", CA 89: 59328d (1978).
Cram, "Binaphthyl-Substituted Macrocyclic Polyethers", CA 82: 73050u (1975).
Timko et al., "Host–Guest Complexation. 10.", CA 90: 23631d (1979).

*Primary Examiner*—Glennon H. Hollrah
*Assistant Examiner*—A. A. Owens
*Attorney, Agent, or Firm*—Flynn, Thiel, Boutell & Tanis

[57] ABSTRACT

A crown ether compound is shown below and useful as a separating agent for chemical compounds.

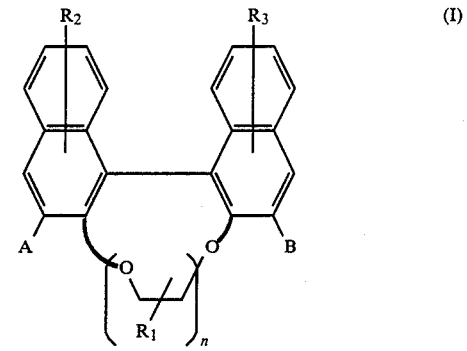

(In the formula, A and B represent hydrogen atoms, straight chain or branched alkyl groups having 1–6 carbon atoms, allyl groups having 6–10 carbon atoms, or aralkyl groups having 7–9 carbon atoms. Although A and B may be different groups, it is preferable that they be the same.

$R_1$ represents a hydrogen atom, a straight chain or branched alkyl group having 1–20 carbon atoms, or preferably an alkyl group having 6–16 carbon atoms. $R_1$ may be bonded to any carbon atom on the cyclical ester group and its number is 1–12, and preferably 1–3. n represents an integer from 3–10, and preferably 4–8, with 5 or 6 being even more preferable.

In addition $R_2$ and $R_3$ represent straight chain or branched alkyl groups having 1–30, and preferably 6–20 carbon atoms, or aryl groups having 6–18 carbon atoms, or aralkyl groups having 7–30 carbon atoms. The location of $R_2$ and $R_3$ may be anywhere other than the A and B substitution positions on the condensed ring, and although one of each of $R_2$ and $R_3$ is satisfactory, a maximum of 5 groups may be substituted. In addition, $R_2$ and $R_3$ may also be different.)

5 Claims, No Drawings

CROWN ETHER COMPOUND AND SEPARATING AGENT

INDUSTRIAL UTILIZATION FIELD

This invention relates to a new crown ether compound. In addition, this invention relates to a separating agent in which said compound is adsorbed onto a carrier, and particularly to a filler for separation of optical isomers.

Crown ether compounds that do not possess substituents $R_2$ and $R_3$ in general formula (I) indicated in the claim of the invention are commonly known. In addition, filling agents for separation of optical isomers that use this are also commonly known (refer to Pat. Disclosure SHO 62-210053).

Notwithstanding, since the adsorption of separating agents which use commonly known crown ether compounds coated on the carrier is weak, these separating agents had the problem of poor durability.

The inventors developed a new crown ether compound in order to solve the related problems and provide a separating agent having superior durability which uses this compound.

In other words, this invention relates to a crown ether compound represented with general formula (I) indicated below.

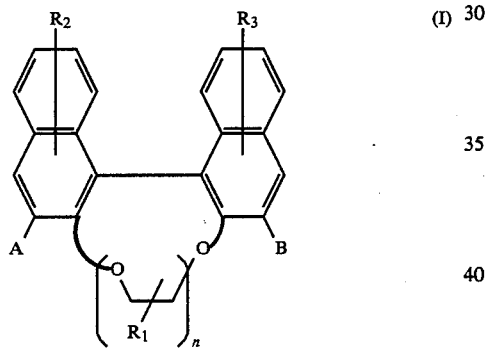

(In the formula, A and B represent hydrogen atoms, straight chain or branched alkyl groups having 1-6 carbon atoms, aryl groups having 6-10 carbon atoms, or aralkyl groups having 7-9 carbon atoms. Although A and B may be different groups, it is preferable that they be the same.

$R_1$ represents a hydrogen atom, or a straight chain or branched alkyl group having 1-20 carbon atoms, or preferably an alkyl group having 6-16 carbon atoms. $R_1$ may be bonded to any carbon atom on the cyclic polyether and its number is 1-12, and preferably 1-3. n represents an integer from 3-10, and preferably 4-8, with 5 or 6 being even more preferable.

In addition, $R_2$ and $R_3$ represent straight chain or branched alkyl groups having 1-30, and more preferably 6-20 carbon atoms, or aryl groups having 6-18 carbon atoms, or aralkyl groups having 7-30 carbon atoms. Although one of each of $R_2$ and $R_3$ is satisfactory, a maximum of 5 groups may be substituted. In addition, $R_2$ and $R_3$ may also be different.)

In general formula (I), A and B represent hydrogen atoms, straight chain or branched alkyl groups having 1-6 carbon atoms such as methyl groups, ethyl groups or isopropyl groups, aryl groups having 6-10 carbon atoms such as phenyl groups, or aralkyl groups having 7-9 carbon atoms such as benzyl groups.

In addition, in general formula (I), $R_2$ and $R_3$ preferably represent alkyl groups having 4-30 carbon atoms such as long-chain alkyl groups such as $C_8$, $C_{12}$, $C_{16}$ or $C_{18}$.

In addition, examples of aryl groups and aralkyl groups include the same examples listed for A and B.

Although $R_2$ and $R_3$ are preferably substituted at the 6,6' position, up to 2-5 groups may also be substituted at other positions.

In other words, the preferable crown ether compound of this invention is indicated with general formula (II) below.

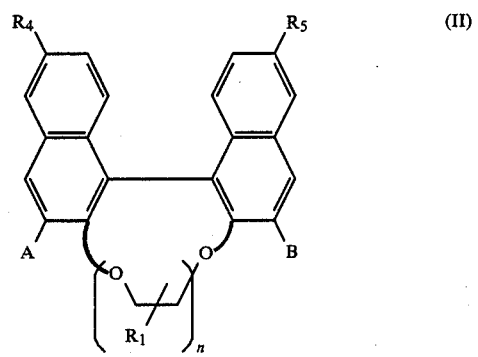

(In the formula, A, B and $R_1$ are the same as those in general formula (I). In addition, $R_4$ and $R_5$ represent straight chain or branched alkyl groups having 4-30 carbon atoms.)

The crown ether compound of this invention indicated in general formulae (I) and (II) may be either racemic or optically active.

In addition, this invention provides a new separating agent. In other words, the separating agent of this invention relates to a separating agent in which the crown ether compound indicated in general formulae (I) and (II) is adsorbed onto a carrier.

SYNTHESIS METHOD

The following scheme is an example of the synthesis method of the new crown ether compound of this invention.

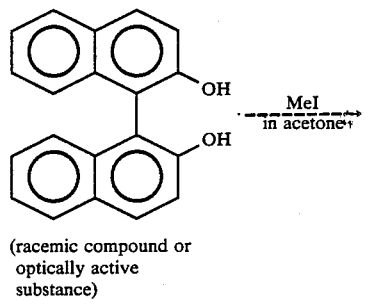

(racemic compound or optically active substance)

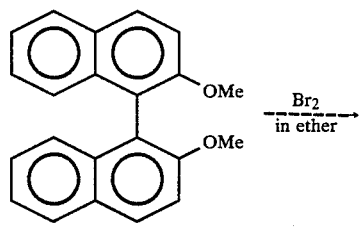
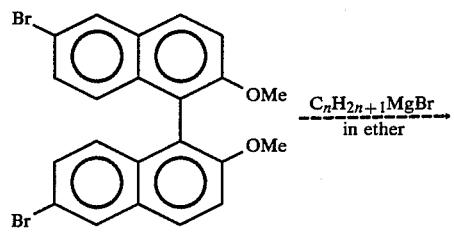
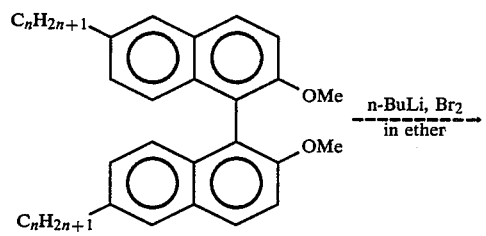
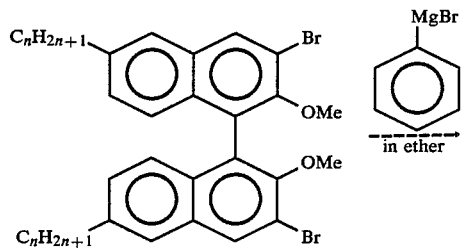
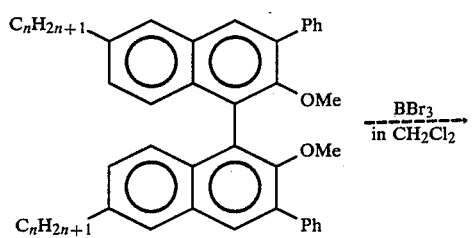
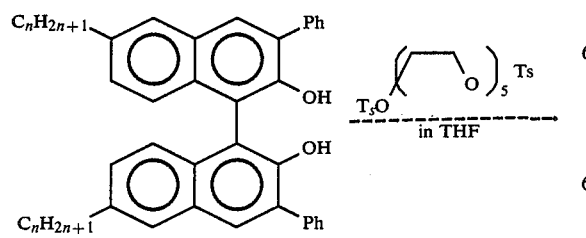

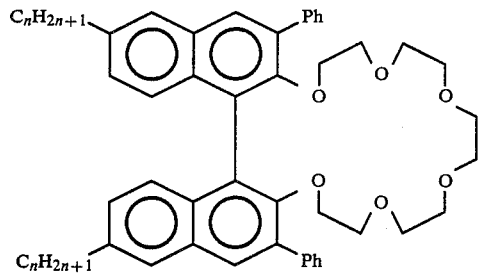

The racemic or optically active crown ether compound in this invention is synthesized, for example, by the procedure indicated below.

First, racemic or optically active binaphthol 1 is used as the starting material. Dialkoxy substance 2 is obtained by reacting this with an excess amount of haloalkyl in an organic solvent such as acetone or tetrahydrofuran in an inert gas atmosphere. Next, by allowing an excess amount of halogen to act on 2 in an organic solvent such as ether or tetrahydrofuran in an inert gas atmosphere, 6,6′ dihalo substance 3 is obtained. When 3 is reacted with a suitable Grignard reagent in an organic solvent like tetrahydrofuran or ether in an inert gas atmosphere, 6,6′ di-substituted substance 4 is obtained. Further, after allowing butyl lithium and tetramethylethylenediamine to act on 4 in an organic solvent like tetrahydrofuran or ether, then reacted with halogen at a low temperature, 3,3′ dihalo substance 5 is obtained. When 5 is reacted with a suitable Grignard reagent in an organic solvent like tetrahydrofuran or ether in an inert gas atmosphere, 3,3′ di-substituted substance 6 is obtained. By allowing boron tribromide to act on 6 in an organic solvent like methylene chloride or chloroform, 2,2′ dihydroxy substance 7 is obtained. By reacting an equimolar amount of penta- or hexaethylene glycol derivative with 7 in an organic solvent like tetrahydrofuran or ether in an inert gas atmosphere, the target compound, crown ether 8 is obtained.

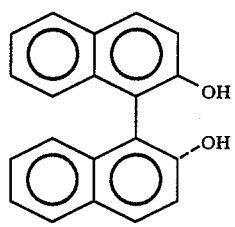

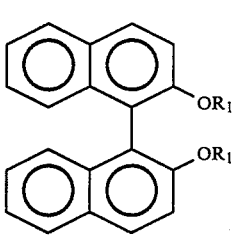

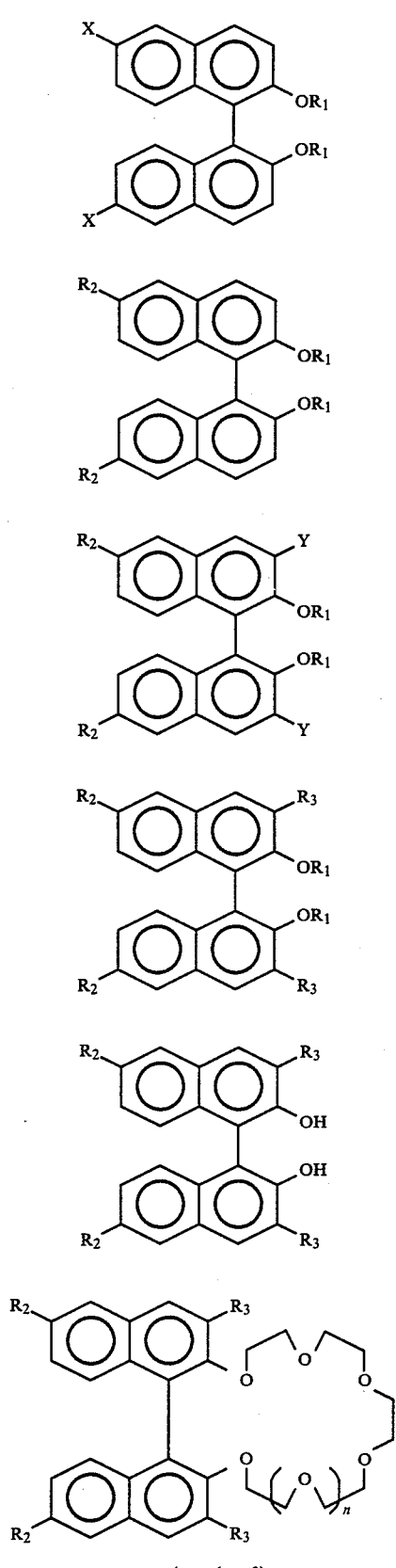

(n = 1 or 2)

SYNTHESIS METHOD OF SEPARATING AGENT

The optically active crown ether compound used in this invention may either of the R or S optical isomers of general formula (I) and (II) indicated previously.

The carrier onto which the above optically active crown compound of this invention is adsorbed and supported on is either a porous organic carrier or porous inorganic carrier. A carrier having a particle diameter of 1–1000 um, and preferably 1–300 um, is used. In addition, it is preferable that the carrier be porous having an average pore diameter of 10Å–10 um, and preferably 50–1000Å. Examples of suitable porous organic carriers include polymer substances such as polystyrene, polyacrylamide and polyacrylate. Examples of suitable porous inorganic carriers include synthetic or natural substances such as silica, alumina, magnesia, titanium oxide, glass, silicate and kaolin.

In addition, in this invention, it is preferable that the above lipophilic optically active crown ether be adsorbed and carried on these carriers treated with a silane treatment agent such as octadecylsilane and diphenyldichlorosilane, or with a silane coupling agent such as phenyldimethoxysilane.

In the adsorbing process onto the carrier on which surface has been treated as above mentioned although there are no particular restrictions on the amount of crown compound that is adsorbed, in order to obtain satisfactory separation results, the amount of crown compound that is adsorbed should be prepared so that $10^{-6}$ to 0.1 moles or less of crown compound are adsorbed per 1 cc of carrier, and preferably $10^{-5}$ to $10^{-3}$ moles per 1 cc of carrier.

In order to perform this adsorption and support satisfactorily, the above surface treated carrier is filled into a column and inside this filled column, a solution in which the above optical active lipophilic crown compound is dissolved in a mixed solvent, consisting of an organic solvent and water having fixed components, is circulated using a pump. In this case, since the concentration of the crown compound in the circulating solution will decrease with time due to adsorption of the crown compound onto the carrier, after a fixed period of time, more water is added to decrease the solubility of the crown compound in the circulating solution followed by repeated circulation in the column. By sequentially repeating this type of procedure, a filler in which the crown compound is adsorbed at a specified concentration can be directly prepared inside the column. Furthermore, the solvent used for the above organic solvent is one that is compatible with water and dissolves the crown compound. Examples of such organic solvent include alcohols such as methanol, ethanol and propanol, as well as other types of solvents such as acetonitrile and tetrahydrofuran.

In addition to the method indicated above, this adsorption can also be performed using a method in which said crown ether is dissolved in a solvent which is able to dissolve it, thoroughly mixing this with the carrier, and then removing the solvent by reduced pressure or pressurized air flow, or using a method in which said crown ether is dissolved in a solvent which is able to dissolve it, thoroughly mixing this with the carrier, and dispersing said solvent by stirring and dispersing in a solution that is not compatible with said solvent.

This column filled with filler in this invention is used for separation of various kinds of racemic compounds.

For example, amino compounds, especially processing asymmetric centers at the [a] and/or [b] positions of the amino group can be separated excellently. Specific examples of such compounds include phenylglycine, methionine, leucine, glutamate, phenylalanine, cysteine, tyrosine, alanine and phenylethylamine. In addition, columns containing the filler of this invention can also be applied in the separation of other optically active organic ions by using ionic interaction.

Although demineralized water, or dilute aqueous solutions of salt or acid are used for the eluate for the column containing the filler of this invention, since dilute acids demonstrate considerable separation effects in particular, these are used preferentially.

EMBODIMENTS

Embodiment 1

A: Synthesis of 6,6'-dioctyl-2,2'-dimethoxy-1,1'-binaphthyl

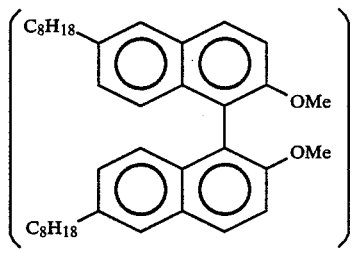

4 ml of bromine was dropped in over a 20 minutes period in a nitrogen atmosphere at −75° C. to a solution (100 ml) of dichloromethane containing 10 g of 2,2'-dimethoxy-1,1'-binaphthyl (R isomer) and allowed to react for 2.5 hours. Following stirring for 30 minutes at a temperature of 25° C., 100 ml of a 10% $Na_2SO_3$ solution was added to decompose the unreacted bromine. 14 g of 6,6'-dibromo-2,2'-dimethoxy-1,1'-binaphthyl (Compound 1) was obtained from the isolated cake-form product and the dried residue resulting from evaporation of the dichloromethane phase (yield: 93%).

63 mmol (100 ml of ether solution) of $C_8H_{17}MgBr$ were added in a nitrogen atmosphere to a ether solution (150 ml) containing 10 g of Compound 1 and 1.25 g of dichloro[1,3-bis(diphenylphosphine)propane]nickel, and refluxed for 20 hours. After cooling down, 800 ml each of dichloromethane and 1M hydrochloric acid were added to obtain an oily reaction product by extraction. By purifying the above reaction product with column chromatography (silica gel, petroleum ether-/ethyl ether), 8.1 g of pure 6,6'-dioctyl-2,2'-dimethoxy-1,1'-binaphthyl (Compound 2) were obtained (yield: 72%).

B: Synthesis of 6,6'-dioctyl-3,3'-diphenyl-2,2'-dihydroxy-1,1'-binaphthyl

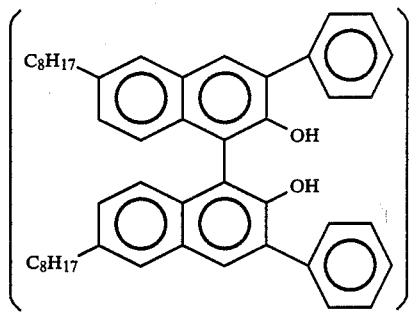

32 ml of 1.6M butyl lithium (hexane solution) were added in a nitrogen atmosphere to 400 ml of an ether solution containing 5.2 g of tetramethylethyleneamine. After allowing to react for 15 minutes at 25° C., an ether suspension containing 6.8 g of Compound 2 was added and stirred for 3 hours. Next, after cooling to −78° C., 10 ml of bromine dissolved in 30 ml of pentane were added over a 10 minutes period. After the reaction liquid was returned to room temperature (25° C.) and stirred for 1 hour, 300 ml of a saturated solution of $Na_2SO_3$ were added and allowed to react for 4 hours. The dichloroethane extract of the mixture was purified with column chromatography (silica gel, cyclohexane/benzene), to give 4.8 g of 6,6'-dioctyl-3,3'-dibromo-2,2'-dimethoxy-1,1'-binaphthyl (Compound 3) (yield: 55%).

20 mmol of phenylmagnesium bromide (PhMgBr) (30 ml of an ether solution) were added in a nitrogen atmosphere to 50 ml of ether in which 4.4 g of Compound 3 and 0.5 g of $Ni[P(C_6H_5)_3]_2Cl_2$ were suspended, and refluxed for 20 hours. After cooling down, 500 ml each of dichloromethane and 1M hydrochloric acid were added and the layers were separated. The organic layer was dried and evaporated under reduced pressure, and residue was purified with column chromatography (silica gel, cyclohexane/benzene) to get 1.66 g of 6,6'-dioctyl-3,3,'-diphenyl-2,2'-dimethoxy-1,1'-diphenyl (Compound 4) (yield: 38%).

1.5 g of Compound 4 were then dissolved in 150 ml of dichloromethane and after cooling to 0° C., 7.5 g of $BBr_3$ were added. This was then allowed to react for 24 hours at 25° C. The reactants were then again cooled to 0° C. and after decomposing the excess $BBr_3$ with water, 6,6'-dioctyl-3,3'-diphenyl-2,2'-dihydroxy-1,1'-binaphthyl (Compound 5) was obtained from the organic layer. This was purified by column chromatography to get 1.55 g (yield: 80%).

C: Synthesis of 2,3:4,5-bis[1,2-(3-phenyl-6-octylnaphtho)]-1,6,9,12,15,18-hexaoxacycloeicosa-2,4-diene

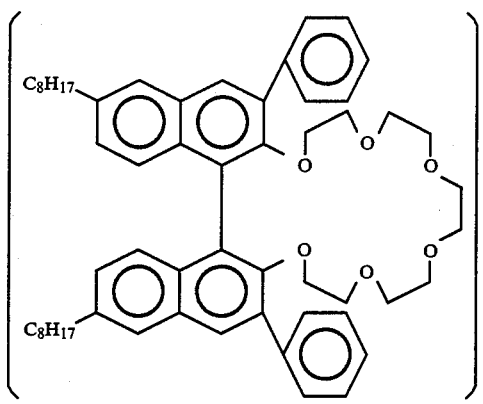

0.24 g of KOH was added in a nitrogen atmosphere at 25° C. to 100 ml of a tetrahydrofuran solution containing 0.74 g of Compound 5 and 0.68 g of pentaethyleneglycol ditosylate, and refluxing for 72 hours. The reactants were extracted with dichloromethane, evaporated under reduced pressure, and purified with column chromatography (silica gel, petroleum ether/ethyl ether) and gel chromatography (polystyrene/chloroform) to get 0.44 g of the desired compound, 2,3:4,5-bis[1,2-(3-phenyl-6-octylnaphtho)]-1,6,9,12,15,18-hexaoxacycloeicosa-2,4-diene (Compound 6) (yield: 46%). The data regarding the physical properties of this Compound 6 is indicated below.

Specific Rotation: $[a]^{25}_{589} = +7.7°$.
Mass Spectrum: m/e 864(M+).
$^1$H NMR (400 MHz, CDCl$_3$)=0.87(t,CH$_3$,6H), 1.29(m,other CH$_2$),20H), 1.70(m, β-CH$_2$,4H), 3.41(m,OCH$_2$,2OH), 7.47(m,ArH,18H).

SEPARATION EXAMPLES

In the tables, $k_D'$, $k_L'$, a and $R_s$ are defined as indicated below.

Capacity Factor ($k_D'$, $k_L'$) =

$$\frac{(\text{Retention Volume of each enantiomer}) - (\text{Dead Volume})}{(\text{Dead Volume})}$$

separation factor ($[a]$) =

$$\frac{\text{Capacity Factor of the later Eluted Enantiomer}}{\text{Capacity Factor of the Earlier Eluted Enantiomer}}$$

Resolution ($Rs$) =

$$\frac{2 \times (\text{Distance between Peaks of the Earlier Eluted Enantiomer and the Later One})}{\text{Total of Bandwidths of Both Peaks}}$$

Separation Example 1

A: Preparation of Optical Isomer Separation Column

80 mg of the optically active R isomer of the crown compound obtained in Embodiment 1 were dissolved in a 95% aqueous methanol solution (60 ml). This solution was then circulated in a commercially available octadecyl silica column (ODS column, Lichrosorb rp-18, diameter: 4 mm, length: 125 mm, particle diameter: 5 um) for 12 hours using a pump. Water was sequentially added to the circulating liquid to gradually reduce the methanol ratio (the final methanol content of the circulating liquid was approx. 70%). As a result, the crown compound was nearly completely adsorbed onto the ODS in the column.

B: Separation of Optical Isomers

The above optical isomer separation column was connected to a HPLC (Nihon Bunko, Model DIP-1 pump, Soma Optical, Model S-3101A UV Detector, Rheodyne sample injector). Examples of separation of racemic amino acids and amines are indicated in Table 1.

In this case, $10^{-2}$M HClO$_4$ was used for the eluate and column temperature were 18° C. and 2° C. In addition, the sample (amino compound) amount was $10^{-8}$ moles. Further, detection of the amino compound was performed with UV absorption at 200 nm or 254 nm.

As is shown in Table 1, the L isomer was eluted before the D isomer for all the amino acids. Conversely, in the case of phenylethylamine, the D isomer was eluted prior to the L isomer. In addition, separation was improved the lower the column temperature. Although more than 20 a-amino acids were investigated, all were optically separated with the exception of proline. The separation factor was dependent upon the concentration of the acid in the eluate. Separation factor increased with increasing concentrations of acid.

Separation Example 2

174 mg of the optically active R isomer of the crown compound obtained in Embodiment 1 were dissolved in a 97% aqueous methanol solution (60 ml). This solution was then circulated in a commercially available octadecyl silica column (ODS column, Lichrosorb rp-18, diameter: 4 mm, length: 125 mm, particle diameter: 5 um) for 12 hours using a pump. Water was sequentially added to the circulating liquid to gradually reduce the methanol ratio (the final methanol content of the circulating liquid was approx. 70%). As a result, the crown compound was nearly completely adsorbed onto the ODS in the column.

This column was attached to the HPLC described in Separation Example 1 and optical separation was performed on the amino acids. Those results are indicated in Table 2 (columns R-2). Table 2 also shows the results when the crown compound (R-1) described in Pat. Disclosure SHO 62-210053 was used as a comparative example.

For the measurement conditions, the column temperature was 18° C., $10^{-2}$M HClO$_4$ was used for the eluate and the sample amount was $10^{-8}$ moles.

In the case a crown compound was used having the same number of moles, as can be seen from the table, the column of this invention (R-2) demonstrated separation capabilities comparable with those of the column of the comparative example (R-1).

Next, the results of an examination of the organic solvent resistance of this column are indicated in Table 3. This column demonstrated organic solvent resistance considerably superior to that of the R-1 column. Even when 40% methanol was used for the eluate, elution of the adsorbed crown compound was not detected at all.

Table 4 indicates the results of optical separation of amino acids when a mixed solution of methanol and water (containing $10^{-2}$M HClO$_4$) was used as the eluate.

As the methanol content of the eluate increased, the retention time of the amino acids decreased (capacity factor) resulting in an increased separation factor.

TABLE 1

Optical Separation of Racemers

| | 18° C. | | | | 2° C. | | | |
|---|---|---|---|---|---|---|---|---|
| | $K_L'$ | $K_D'$ | α | $R_S$ | $K_L'$ | $K_D'$ | α | $R_S$ |
| Alanine | 0.31 | 0.51 | 1.64 | 0.97 | 0.48 | 0.98 | 2.04 | 2.44 |
| valine | 1.18 | 1.18 | 1.00 | — | 1.35 | 1.49 | 1.10 | 0.45 |
| Norvaline | 1.38 | 1.91 | 1.39 | 2.15 | 1.73 | 2.90 | 1.67 | 3.85 |
| Leucine | 4.09 | 5.32 | 1.30 | 2.79 | 4.70 | 7.09 | 1.51 | 4.21 |
| Norleucine | 4.50 | 5.93 | 1.32 | 2.64 | 5.62 | 8.54 | 1.52 | 4.40 |
| a-Amino Butyrate | 0.60 | 0.76 | 1.27 | 0.71 | 0.64 | 1.01 | 1.57 | 1.79 |
| Isoleucine | 3.23 | 3.51 | 1.09 | 0.76 | 3.92 | 4.48 | 1.14 | 1.32 |
| Phenylalanine | 12.62 | 13.83 | 1.10 | 1.17 | 18.52 | 20.93 | 1.13 | 1.55 |
| DOPa | 5.52 | 6.12 | 1.11 | 1.15 | 12.76 | 14.53 | 1.14 | 1.53 |
| Phenylglycine | 2.45 | 8.27 | 3.37 | 8.63 | 3.19 | 19.32 | 6.06 | 14.47 |
| Methionine | 2.29 | 3.72 | 1.63 | 3.99 | 3.33 | 7.08 | 2.12 | 6.99 |
| Threonine | 0.21 | 0.30 | 1.44 | 0.37 | 0.27 | 0.58 | 2.17 | 1.61 |
| Cysteine | 0.31 | 0.44 | 1.43 | 0.46 | 0.42 | 0.79 | 1.89 | 1.50 |
| Tyrosine | 9.42 | 10.24 | 1.09 | 1.04 | 20.74 | 22.97 | 1.11 | 1.22 |
| Asparginate | 0.23 | 0.40 | 1.76 | 0.54 | 0.43 | 0.80 | 1.84 | 1.68 |
| Glutamate | 0.43 | 0.83 | 1.91 | 1.69 | 0.75 | 3.25 | 4.33 | 7.92 |
| Glutamine | 0.23 | 0.64 | 2.75 | 1.97 | 0.40 | 1.75 | 4.37 | 4.98 |
| Lysine | 0.81 | 0.81 | 1.00 | — | 2.00 | 2.36 | 1.18 | 0.97 |
| Arginine | 0.47 | 0.81 | 1.73 | 1.61 | 0.92 | 2.40 | 2.60 | 4.11 |
| Phenylethylamine | 19.70 | 17.37 | 1.13 | 0.77 | 22.85 | 27.66 | 1.21 | 1.67 |
| a-Amino-Caprolactam | 1.31 | 1.86 | 1.42 | 2.13 | 1.81 | 3.15 | 1.74 | 3.88 |

TABLE 2

Optical Separation of Amino Acids and Racemers

| | R-1 | | | | R-2 | | | |
|---|---|---|---|---|---|---|---|---|
| | $K_L'$ | $K_n'$ | α | $R_S$ | $K_L'$ | $K_n'$ | α | $R_S$ |
| Alanine | 0.05 | 1.02 | 2.03 | 2.09 | 0.56 | 1.04 | 1.86 | 1.73 |
| valine | 0.98 | 1.22 | 1.25 | 0.86 | 0.88 | 1.02 | 1.16 | sh |
| Methionine | 2.26 | 5.90 | 2.61 | 4.68 | 2.16 | 4.61 | 2.14 | 3.03 |
| Phenylalanine | 8.73 | 13.22 | 1.51 | 2.33 | 7.59 | 9.49 | 1.25 | 1.11 |
| Phenylglycine | 2.81 | 17.54 | 6.25 | 7.39 | 2.70 | 12.76 | 4.73 | 6.56 |
| Threonine | 0.31 | 0.53 | 1.69 | 1.08 | 0.32 | 0.59 | 1.86 | 1.26 |
| Tyrosine | 6.15 | 9.39 | 1.53 | 2.38 | 6.29 | 8.13 | 1.29 | 1.03 |
| Glutamate | 0.59 | 2.34 | 3.95 | 5.05 | 0.66 | 2.38 | 3.63 | 3.87 |
| Arginine | 0.71 | 1.36 | 1.93 | 2.10 | 0.88 | 1.80 | 2.06 | 1.75 |

TABLE 3

Column Organic Solvent Resistance

| Column | 0% MeOH | 10% MeOH | 20% MeOH | 30% MeOH | 40% MeOH |
|---|---|---|---|---|---|
| R-1 | — | $3.5 \times 10^{-7}$ | $6.7 \times 10^{-7}$ | $9.6 \times 10^{-6}$ | $1.5 \times 10^{-4}$ |
| R-2 | — | — | — | — | — |

TABLE 4

Optical Separation of Amino Acids Using Methanol-Containing Eluate

| | | 0% MeOH | | | 10% MeOH | | | 20% MeOH | | | 30 MeOH | | | 40% MeOH | | |
|---|---|---|---|---|---|---|---|---|---|---|---|---|---|---|---|---|
| | | k' | α | Rs | k' | α | Rs | k' | α | Rs | k' | α | Rs | k' | α | Rs |
| Glutamate | L | 0.61 | 3.63 | 3.87 | 0.58 | 4.17 | 3.65 | 0.54 | 4.78 | 3.61 | 0.53 | 5.15 | 4.12 | 0.50 | 5.41 | 4.02 |
| | D | 2.38 | | | 2.42 | | | 2.60 | | | 2.74 | | | 2.73 | | |
| Arginine | L | 0.88 | 2.06 | 1.75 | 0.63 | 2.27 | 1.75 | 0.47 | 2.39 | 1.83 | 0.39 | 2.50 | 1.79 | 0.33 | 2.53 | 1.56 |
| | D | 1.80 | | | 1.43 | | | 1.13 | | | 0.97 | | | 0.83 | | |
| Methionine | L | 2.16 | 2.14 | 3.03 | 1.60 | 2.50 | 3.34 | 1.35 | 3.00 | 3.45 | 1.17 | 3.48 | 3.82 | 1.01 | 3.91 | 3.58 |
| | D | 4.61 | | | 4.01 | | | 4.06 | | | 4.08 | | | 3.96 | | |
| Phenylglycine | L | 2.70 | 4.73 | 6.56 | 2.00 | 5.69 | 6.11 | 1.78 | 6.71 | 5.82 | 1.39 | 7.88 | 5.56 | 1.14 | 8.64 | 5.05 |
| | D | 12.76 | | | 11.39 | | | 11.92 | | | 10.97 | | | 9.82 | | |
| Phenylalanine | L | 7.59 | 1.25 | 1.11 | 4.32 | 1.37 | 1.38 | 3.04 | 1.54 | 1.70 | 2.11 | 1.79 | 1.98 | 1.56 | 2.00 | 1.91 |
| | D | 9.49 | | | 5.90 | | | 4.68 | | | 3.77 | | | 3.12 | | |
| Tyrosine | L | 6.29 | 1.29 | 1.03 | 3.17 | 1.49 | 1.57 | 2.23 | 1.75 | 1.92 | 1.50 | 2.05 | 2.27 | 1.12 | 2.28 | 2.19 |
| | D | 8.13 | | | 4.72 | | | 3.90 | | | 3.08 | | | 2.56 | | |
| Tryptophan | L | 47.70 | 1.15 | 0.73 | 21.45 | 1.27 | 1.24 | 12.52 | 1.44 | 1.58 | 7.26 | 1.66 | 1.80 | 4.55 | 1.89 | 1.68 |
| | D | 54.89 | | | 27.25 | | | 17.98 | | | 12.07 | | | 8.59 | | |

Embodiment 2

A: Synthesis of 6,6'-dioctadecyl-2,2'-dimethoxy-1,1'-binaphthyl 4 ml of bromine was dropped into a dichloromethane solution containing 10 g of 2,2'-dimethoxy-1,1'-binaphthyl (S isomer) over a 20 minutes period in a 0° C. nitrogen atmosphere, and allowed to stir for 30 minutes. 60 ml of 20% $NaHSO_3$ were then added to decompose the unreacted bromine. 200 ml of water were added to the reaction solution and after vigorous stirring, the solution was filtered with a glass filter with the residue then washed with methylene chloride (1). After separating off the mother liquor, the organic phase was evaporated under reduced pressure. 20 ml of chloroform were added to the residue, filtered, and washed with chloroform(2). The filtrate was evaporated and purified with column chromatography (silica gel, chloroform/hexane) (3). As a result of NMR and mass spectroscopy, (1), (2) and (3) were all the target substances. The amount obtained was 12.8 g and the yield was 83.6% (Compound 1).

80 ml of dry ether were added to 1.65 g of magnesium and a solution in which 22 g of stearyl bromide were dissolved in 60 ml of ether in a nitrogen atmosphere was slowly dropped in. Following dropping, the solution was cooled after refluxing while heating for 1 hour. A suspension of 4 g of Compound 1 and 320 mg of dichloro[1,3-bis(diphenylphosphine)propane]nickel in 150 ml of ether were added and refluxed for 2 hours. After cooling down 50 ml of water and 70 ml of 1N hydrochloric acid were added. After stirring for 1 hour, extracted with 200 ml of 0.5N hydrochloric acid and 400 ml of chloroform. The organic layer was dried and evaporated under reduced pressure and purified with column chromatography (silica gel, chloroform/hexane) to get the pure reaction product. The amount obtained was 5.4 mg and the yield was 78% ($[a]^D = +9.05$ (c=1.05 in THF) (Compound 2).

B: Synthesis of 6,6'-dioctadecyl-3,3'-diphenyl-2,2'-dihydroxy-1,1'-binaphthyl 3.1 ml of tetramethylethylenediamine and 12 ml of n-BuLi were added to 100 ml of dry ether and stirred for 20 minutes in a nitrogen atmosphere at room temperature. 5.2 g of Compound 2 were added to this followed by additional stirring for 20 minutes at room temperature and it completely decomposed resulting in a wine red-colored homogeneous solution. This solution was cooled to $-50°$ C. followed by slowly dropping in a solution of 3 ml of bromine diluted in 50 ml of hexane. After stirring for 20 minutes as is, the temperature of the solution was gradually returned to room temperature. Once at room temperature, the unreacted bromine was dissolved with a saturated aqueous solution of sodium sulfite. The product was then extracted with chloroform and purified with column chromatography (silica gel, chloroform/hexane) to get 1.99 g of pure 6,6'-dioctadecyl-3,3'-dibromo-2,2'-dimethoxy-1,1'-binaphthyl. (yield 32%) (Compound 3).

A suspension of 80 mg of Ni[PPh$_3$]$_2$Cl$_2$ and 20 ml of ether were added to 1.9 g of Compound 3, and stirred for 15 minutes in a nitrogen atmosphere. 10 mmol of phenylmagnesium bromide were added and refluxed for 4 hours. After cooling down, the solution was quenched with 20 ml of 1N hydrochloric acid and extracted with chloroform. The organic layer was evaporated under reduced pressure, and purified with column chromatography (silica gel, hexane/benzene) to get 670 mg of pure 6,6'-dioctadecyl-3,3'-diphenyl-2,2'-dimethoxy-1,1'-binaphthyl. (yield 36%) (Compound 4).

20 ml of methylene chloride were added to 670 mg of Compound 4. Following addition of 2 ml of BBr$_3$ at 0° C. in a nitrogen atmosphere, the solution was stirred for 6 hours at room temperature. After quenching the reaction solution with 30 ml of water, the solution was extracted with chloroform and purified with column chromatography (silica gel, hexane/benzene) to get 560 mg of pure 6,6'-dioctadecyl-3,3'-diphenyl-2,2'-dihydroxy-1,1'-binaphthyl with a yield of 86% (Compound 5).

C: Synthesis of 2,3:4,5-bis[1,2-(3-phenyl-6-octadecylnaphtho)]1,6,9,12,15,18-hexaeicosa-2,4-diene 520 mg of Compound 5 were dissolved in 100 ml of THF in a nitrogen atmosphere followed by the addition of 0.25 g of KOH and 330 mg of pentaethylene glycol ditosylate. After refluxing for 72 hours, the product was extracted with chloroform and purified with column chromatography (alumina, chloroform/hexane) to get 320 mg of the pure target compound. The yield was 51%.

Specific Rotation: $[a]^D = -8.5$, $[a]^{577} = -7.7$, $[a]^{546} = -8.5$, $[a]^{435} = -11.7$ (c=1.01 in THF).

Mass Spectrum: m/e 1144 (M+).

$^1$H NMR (60 MHz,CDCl$_3$): =0.86(t,CH$_3$,6H), 1.23(m,other CH$_2$,64H), 2.72(t,a-CH$_2$,4H) 3.27(m,OCH$_2$,2OH), 7.42(m,ArH,18H).

Embodiment 3

A: Preparation of Optical Isomer Separation Column 104 mg of 2,3:4,5-bis[1,2-(3-phenyl-6-octadecylnaphtho)] 1,6,9,12,15,18-hexaeicosa-2,4-diene were dissolved in a solvent mixture of 27 ml of methanol and 10 ml of THF. This solution was then circulated a column (inner diameter: 4 mm, length: 125 mm) filled with commercially available octadecyl silica (ODS, particle diameter: 5 u) using a high-pressure pump, and allowed to circulate inside the column for 6 hours. Water was sequentially added to the circulating liquid and gradually decrease the ratio of organic solvent. As a result, the above substance was nearly completely adsorbed onto the ODS in the column.

B: Separation of Optical Isomers

An example of optical resolution of racemic amino acids with a HPLC is indicated in Table 5. In this case, a pH 2.0 aqueous solution of perchloric acid was used for the eluate, column temperature were 18° C. and 2° C., 2 ul of the sample were injected at a concentration of 5 mM, and the sample was detected by UV absorption at 200 nm.

TABLE 5

|  | 2° C. 0.5 ml/min. | | | | 18° C. 0.5 ml/min. | | | |
| --- | --- | --- | --- | --- | --- | --- | --- | --- |
|  | $k^1$ | $k^2$ | a | RS | $k^1$ | $k^2$ | a | RS |
| Alanine | 0.49 | 0.86 | 1.76 | 1.82 | 0.33 | 0.48 | 1.44 | 1.00 |
| Valine | 1.01 | 1.01 | 1.0 | — | 0.82 | 0.82 | 1.0 | — |
| Leucine | 3.14 | 4.45 | 1.42 | 1.76 | 2.45 | 3.08 | 1.26 | 1.20 |
| Isoleucine | 2.55 | 2.93 | 1.15 | 0.66 | 2.05 | 2.05 | 1.0 | — |
| Phenylalanine | 11.69 | 13.20 | 1.13 | 1.40 | 6.78 | 6.78 | 1.0 | — |
| DOPA | 8.92 | 10.16 | 1.14 | 0.79 | 3.67 | 4.01 | 1.09 | 1.03 |
| Methionine | 2.37 | 4.60 | 1.94 | 2.90 | 1.51 | 2.27 | 1.51 | 2.07 |
| Phenylglycine | 2.34 | 11.35 | 4.85 | 4.26 | 1.63 | 4.63 | 2.84 | 3.76 |
| Serine | 0.30 | 0.40 | 1.32 | 0.98 | 0.25 | 0.25 | 1.0 | — |
| Threonine | 0.31 | 0.55 | 1.75 | 1.39 | 0.32 | 1.32 | 1.0 | — |
| Tyrosine | 13.71 | 14.92 | 1.09 | 1.82 | 5.63 | 5.63 | 1.0 | — |
| Asparagine | 0.30 | 0.40 | 1.32 | 1.20 | 0.25 | 0.25 | 1.0 | — |
| Asparginate | 0.47 | 0.70 | 1.62 | 1.47 | 0.29 | 0.29 | 1.0 | — |
| Glutamate | 0.69 | 2.47 | 3.60 | 3.75 | 0.41 | 0.96 | 2.33 | 2.17 |
| Ornithine | 0.85 | 1.23 | 1.44 | 1.06 | 0.49 | 0.49 | 1.0 | — |
| Lysine | 1.60 | 1.79 | 1.12 | 0.93 | 0.67 | 0.67 | 1.0 | — |
| Arginine | 0.71 | 0.71 | 2.42 | 2.32 | 0.42 | 0.67 | 1.58 | 1.07 |
| Histidine | 0.46 | 0.46 | 1.0 | — | — | — | 1.0 | — |
| Tryptophan | 95.99 | 95.55 | 1.0 | — | 37.59 | 37.59 | 1.0 | — |
| Glutamine |  |  |  |  |  |  |  |  |

We claim:

1. A racemic or optically active crown ether compound having the formula

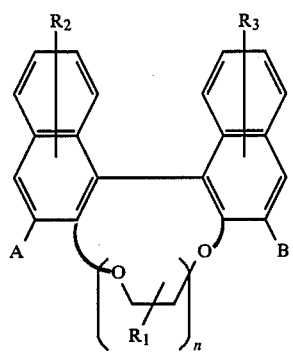

wherein A and B, which can be the same or different, are hydrogen, straight chain or branched alkyl having from 1 to 6 carbon atoms, aryl having from 6 to 10 carbon atoms, or aralkyl having from 7 to 9 carbon atoms, $R_1$ is hydrogen or straight chain or branched alkyl having from 1 to 20 carbon atoms, wherein $R_1$ can be bonded to any carbon atom on the cyclic polyether and the number of $R_1$ groups is from 1 to 12, and n is an integer of from 3 to 10, and $R_2$ and $R_3$, which can be the same or different, are straight chain or branched alkyl having from 1 to 30 carbon atoms, aryl having 6 to 18 carbon atoms, or aralkyl having 7 to 30 carbon atoms, wherein $R_2$ and $R_3$ can be located anywhere other than at the A and B substitution positions on the condensed ring, and the sum of the number of the $R_2$ and $R_3$ groups is from 2 to 5.

2. A racemic or optically active crown ether compound having the formula wherein A and B, which can be the same or different, are hydrogen, straight chain or branched alkyl having from 1 to 6 carbon atoms, aryl having from 6 to 10 carbon atoms, or aralkyl having from 7 to 9 carbon atoms, $R_1$ is hydrogen or straight chain or branched alkyl having from 1 to 20 carbon atoms, wherein $R_1$ can be bonded to any carbon atom on the cyclic polyether and the number of $R_1$ groups is from 1 to 12, n is an integer of from 3 to 10, and $R_4$ and $R_5$ are straight-chain or branched alkyl having from 4 to 30 carbon atoms.

3. A separating agent comprising the optically active crown ether compound claimed in claim 1, adsorbed onto a carrier.

4. A separating agent comprising the optically active crown ether compound claimed in claim 3, adsorbed onto a carrier.

5. The racemic or optically active crown ether compound of claim 1 in which A and B are the same, $R_1$ is alkyl having from 6 to 16 carbon atoms, the number of $R_1$ groups is from 1 to 3, n is an integer of from 4 to 8, and $R_2$ and $R_3$ are alkyls having from 6 to 20 carbon atoms.

* * * * *